United States Patent [19]

Stutzman

[11] Patent Number: Plant 6,420

[45] Date of Patent: Nov. 22, 1988

[54] DIEFFENBACHIA NAMED "MILLIE WHITE"

[75] Inventor: Donald J. Stutzman, Longwood, Fla.

[73] Assignee: A. Duda & Sons, Inc., Oviedo, Fla.

[21] Appl. No.: 650,780

[22] Filed: Apr. 11, 1986

[51] Int. Cl.[4] ..... A01H 5/00

[52] U.S. Cl. ..... Plt./88

[58] Field of Search ..... Plt./88

[56] References Cited

U.S. PATENT DOCUMENTS

P.P. 4,504 2/1980 Welker ..... Plt. 88

*Primary Examiner*—Robert E. Bagwill

*Attorney, Agent, or Firm*—Rohm & Monsanto

[57] ABSTRACT

A new cultivar of Dieffenbachia characterized by a dark green, irregular margin, enclosing an almost white to delicate light green interior, sprinkled with irregular spots of dark green. Midrib and veins show a prominent white coloration in vivid contrast to interveinal areas. Type of growth is erect, compact, and vigorous.

2 Drawing Sheets

BACKGROUND OF THE NEW PLANT

The present invention relates to a new cultivar of Dieffenbachia which was discovered in May 1982 as a sport from the variety "Perfection." The plant described herein is possessed of exceptional color and appearance, and has been asexually propagated under my direction for the past 3½ years in a nursery at Apopka, Fla. Repeated propagations by tip cuttings for some fifteen generations have demonstrated the stability of the genetic characteristics of this new plant.

BRIEF DESCRIPTION OF THE DRAWING

Comprehension of the color and other visual aspects of the inventive plant is facilitated by reading the following description in conjunction with the annexed color photographs, in which.

DESCRIPTION OF THE NEW PLANT

Figure 1:
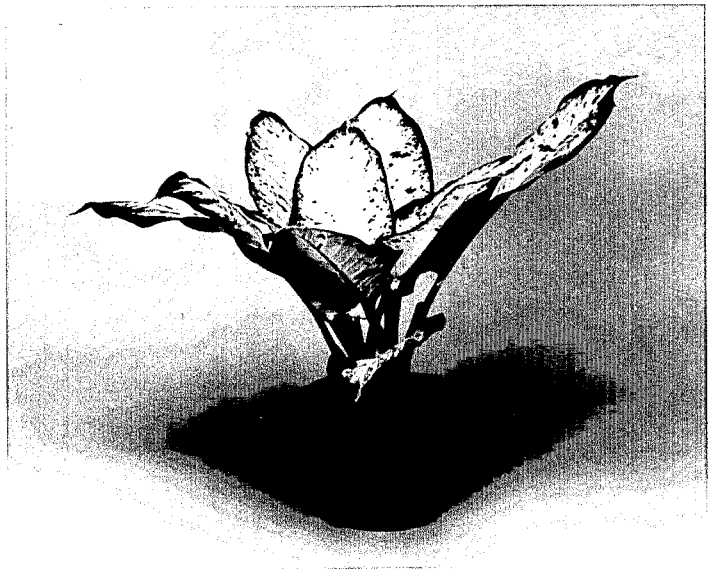
FIG. 1 is a color photograph of a side view of the novel Dieffenbachia plant of the present invention.
Figure 2:
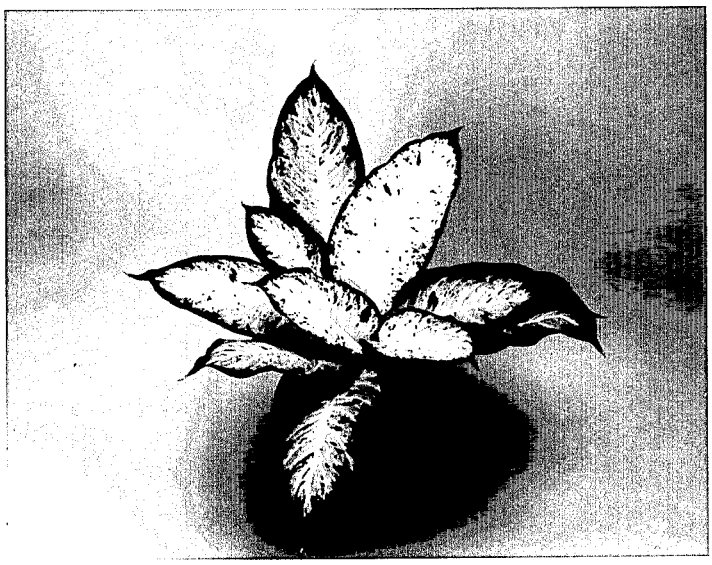
FIG. 2 is a top view of the plant of FIG. 1.
Figure 3:
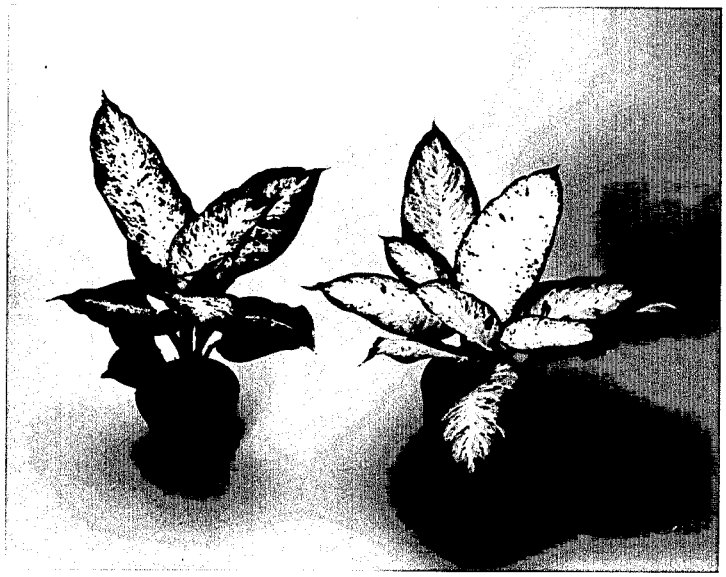
FIG. 3 is an elevated view of a prior Dieffenbachia plant, known as "Perfection," in the left of the photograph, and the new sport in the right.
Figure 4:
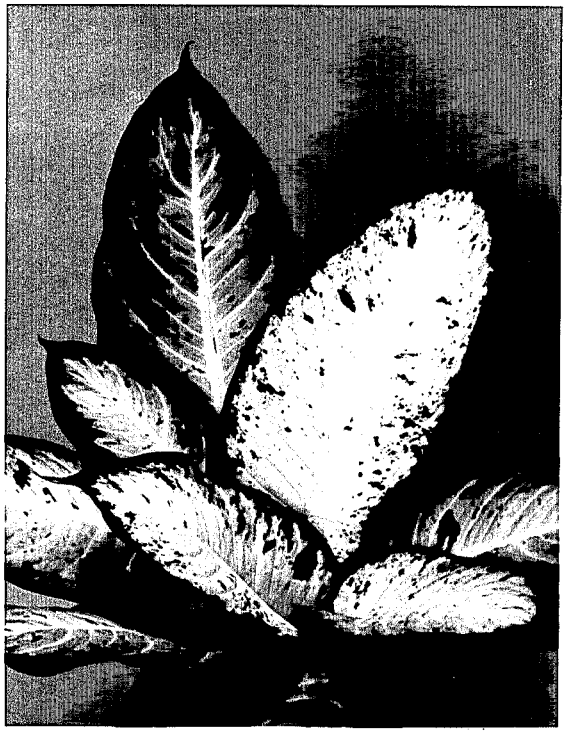
FIG. 4 is a photograph showing a close-up of the plant of the present invention.

Origin: Sport off of "Perfection" 137B.

Parentage: Dieffenbachia "Perfection" 137B, not patented.

Classification:

*Family.*—Araceae (Arum family). Sport from "Perfection" 137B which was tissue cultured from *Dieffenbachia maculata* variety Perfection.

Form: Erect, compact growth type with nodes one inch or less apart, giving 10–11 leaves on a plant 9–10 inches medium (soil) line to bud point. Moderate base sucker production.

Growth rate: Good. Equal to or better than parent variety "Perfection."

Foliage: Excellent (see "Form" description above). Size (height) of plant determines number and size of leaves.

Size and shape of leaves: On plants approximately 10 inches medium (soil) line to buds, upper leaves are some 5×11 inches (leaf blade only) giving a plant about 22 inches medium line to plant tip.

*Shape of leaves.*—Lance-ovate.

Petioles: Depending on location on stem, petioles vary from 4½ to 6 inches in length (higher leaves, longer petioles) making the entire leaf approximately 17 inches for an upper leaf on a "mature" plant.

Texture and appearance: Leaves are relatively smooth though with some rugose growth. The overall growth gives a glossy and smooth appearance.

Midrib of leaves: Midribs have a prominent appearance due to growth structure. Color of the midrib is mainly white but some with delicate tints of light green, or with streaks of light to moderate green.

Leaf blade (minus midrib): Starting next to the midrib is often white or creamy, but usually is a delicate light green. As distance from the midrib increases, the green increases with the light green becoming deeper and more prominent until it meets the dark green spots scattered through the outer portions of the leaves, or until it meets the deep, dark green area along the leaf margin. The deep, dark green mentioned above extends entirely around the leaf margin and varies in thickness from ¼ to 1 inch or more. Inside the irregular dark green margins are small to large irregular splotches of similar dark green tissue.

Characteristics of leaves: Leaf shape is lance-ovate; venation is pinnate; margin, entire; surface, gabrous. Lower surface of leaf is similar to upper surface but less spectacular, and with more green coloration of the midribs.

Stem: Approximately one inch thick at medium line in plant 20 to 24 inches high, medium line to leaf tip, giving a good sturdy base and support to the plant.

Flower: Plant has not bloomed.

The following is a tabulation of the color variation of the plant of the present invention according to *The Munsell Limit Color Cascade* (Munsell Color, Macbeth Color & Photometry Division, 2441 N. Calvert St., Baltimore, Md. 21218) The results of the tabulation were obtained in daylight, 10–12 a.m., Dec. 4, 1985.

| | upper side | under side |
|---|---|---|
| Leaf, younger mature | | |
| Lightest area (whitest) | 21–1 | 21–1 |
| Light green area | 21–2.5 | 21–2 |
| Dark green area | 19–15 | 19–14.5 |
| Leaf, older mature | | |
| Lightest area (whitest) | 21–1 | 21–1.5 |
| Light green area | 21–2.5 | 21–2 |
| Dark green area | 19–15 | 19–14.5 |
| Leaf, immature | | |
| Essentially the same coloration as young mature leaf, except smaller in size. | | |
| Petiole 22–10 | | |

-continued

| Leaf veination | young mature | older mature |
|---|---|---|
| Upper side | | |
| Midrib | 21–1 | 21–1.5 |
| Veins | 21–1 | 21–2 |
| Under side | | |
| Midrib | 22–8 | 21–9.5 |
| Veins | 22–1 | 22–2 |
| Stem 20–9.5 | | |

Although the inventive plant has been described in terms of specific embodiments, it is to be understood that the photographic figures and the description herein are proffered to facilitate comprehension of the invention, and should not be construed to limit the scope thereof.

What is claimed is:

1. A new and distinct variety of Dieffenbachia plant, substantially as shown and described herein.

* * * * *